United States Patent [19]

Dageforde

[11] 4,187,162

[45] Feb. 5, 1980

[54] ELECTROCHEMICAL CELL

[75] Inventor: Allen F. Dageforde, Orange, Calif.

[73] Assignee: Rosemount Inc., Eden Prairie, Minn.

[21] Appl. No.: 918,856

[22] Filed: Jun. 26, 1978

[51] Int. Cl.$^2$ .......................................... G01N 27/40
[52] U.S. Cl. ................................................ 204/195 P
[58] Field of Search ............................. 204/195 P, 1 P

[56] References Cited

U.S. PATENT DOCUMENTS

| | | | |
|---|---|---|---|
| 3,227,643 | 1/1966 | Okun et al. | 204/195 P |
| 3,440,525 | 4/1969 | Cardeiro | 324/30 |
| 3,503,861 | 3/1970 | Volpe | 204/195 P |
| 3,539,455 | 11/1970 | Clark | 204/1 T |
| 3,718,563 | 2/1973 | Krull et al. | 204/195 P |
| 3,855,096 | 12/1974 | Bergman | 204/195 P |

FOREIGN PATENT DOCUMENTS 1260199 2/1968 Fed. Rep. of Germany ........... 204/195
1917179 10/1970 Fed. Rep. of Germany ........... 204/195

Primary Examiner—Howard S. Williams
Attorney, Agent, or Firm—Kinney, Lange, Westman and Fairbairn

[57] ABSTRACT

The present invention is directed to certain modifications to sensor cells to minimize electrolyte dilution or loss and to reduce electrical noise. These objectives are attained by designing and constructing the cell in such a manner as to force the electrolyte to communicate between the anode and cathode by diffusion through a porous plug which is placed adjacent the cathode and in contact with the required porous membrane.

5 Claims, 2 Drawing Figures

ELECTROCHEMICAL CELL

BACKGROUND OF THE INVENTION

The present invention is directed to sensoring apparatus which find utility in measuring various aspects of liquid mediums. More specifically, the invention provides a means of enhancing the effectiveness of an amperometric sensor which utilizes a semi-permeable membrane to separate the internal elements and the electrolyte contained therein (and enveloping the elements) from the media being sampled, monitored or analyzed. In this regard reference is hereby made to U.S. Pat. Nos. 3,510,421; 3,577,332; and 3,929,603 which are hereby incorporated by reference and which comprehensively describe the type of measurements or analysis which are commonly made utilizing these means. In addition, these patents also disclose the type membranes commonly used in the sensors.

With respect to certain type sensors, particularly the halogen sensing cells, the present inventor determined that certain problems existed which effected the overall accuracy and measuring sensitivities. These problems were due, it was discovered, to a defect in the sensors; namely, a loss in the electrolyte concentration within the cell due to the electrolyte's flow from the cell through the membrane to the medium which contained the ion to be measured, and the resulting dilution (as the medium flowed inward through the membrane to replace the lost electrolyte). Cells that were constructed which provided a simple open path between the cathode and anode exhibited short life because of the aforementioned occurrences. It also was noted that these sensors provided "noisy outputs", i.e., electronic noise in the nature of spurious signals, which effected the overall sensitivity and accuracy of the measuring device.

Generally, the present inventor discovered that if the electrolyte contained within the cell reservoir was forced to communicate between the anode and cathode of the cell by diffusion through a porous material (plug) placed adjacent to the cathode and in contact with the cell's membrane, not only was electrolyte concentration loss or dilution controlled but also electronic noise was substantially eliminated. The invention will become more apparent from the description of a typical arrangement of the cell parts which follows, together with the descriptive matter directed to the improvement. Also, the description of the cell as per the explanation of the drawing will serve to highlight the invention.

The cell comprises
(i) an electrically non-conductive body having an electrolytic reservoir therein,
(ii) a pair of spaced electrodes positioned in said reservoir and adapted to be joined by an electrolyte in said reservoir,
(iii) an opening communicating between said reservoir and the exterior of said body,
(iv) a thin flexible polymeric membrane permeable to said constituent and said electrolyte, and
(v) mounting means maintaining said membrane under tension over one electrode which is supported in the face of the electrically non-conductive element which is disposed in said opening and which is in a position to close said opening, wherein said opening is slightly larger than said electrode and the face of the electrically non-conductive element supporting such and the portion of the opening remaining being fitted with a porous material to provide a tightly fitting barrier between said membrane, said electrolyte in said reservoir and said electrodes, and said porous material preferably but not necessarily contacting said membrane and being permeable to said electrolyte so as to permit electrical communication between said electrodes.

SPECIFIC EMBODIMENT

Figure 1:
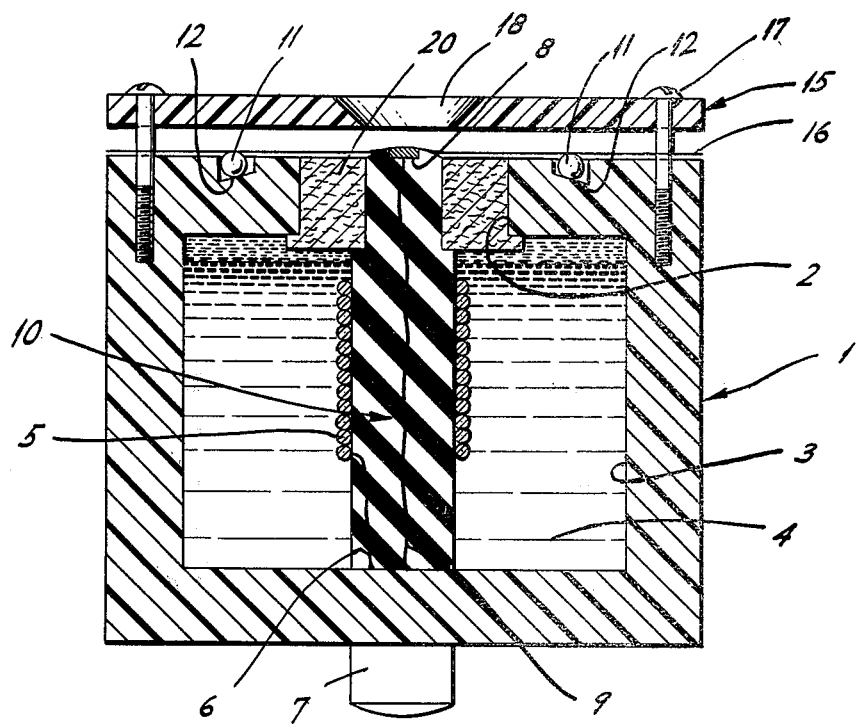
FIG. 1 is an enlarged vertical cross sectional view of the electrochemical cell made according to the present invention.

The cell is composed of cylindrical, electrically nonconductive body 1 and mounting means of cap 15. Body 1 has opening 2 and reservoir 3 which contains electrolyte 4. Electrode 5 (normally the anode) is depicted in the form of a helical wire but may be an embedded electrode and is wrapped around central electrically nonconductive element 10 which leads to terminal 7 or a satellite electrical connection means. Electrode 8 (normally the cathode) is embedded in and flush with the end of element 10. Electrodes 5 and 8 are connected to terminal 7 by means of conductors 6 and 9 respectively. Terminal 7 includes well known appropriate electrical connections, not shown, for connecting the cell to an external circuit. Body 1 contains grooves 12 fitted with O-rings 11 which allow cap or mounting means 15 to securely fasten and tension membrane 16 against electrode 8 and body 1. The grooves 12 are depicted as being angled approximately 10° in accordance with the invention of U.S. Pat. No. 3,887,194, which is hereby incorporated by reference. Fitted annularly and tightly against element 10 bearing cathode 8 is porous plug 20 which is also positioned so as to fill the portion of opening 2 which is not filled by element 10 bearing cathode 8. As will be observed from the drawing, porous plug 20 is fitted so as to require the electrolyte to diffuse through such in order to provide the communication necessary between electrodes 8 and 5 by electrolyte 4. Additionally, since plug 20 is fitted tightly to the body and element 10, escape or dilution of the electrolyte 4 is minimized.

Figure 2:
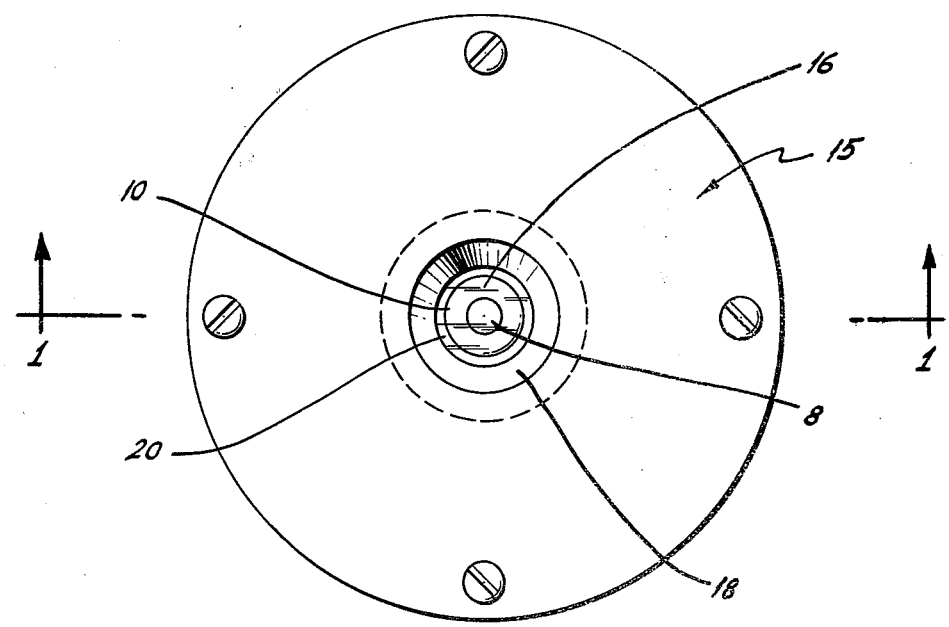
FIG. 2 is a top plan view of the cell of FIG. 1.

FIG. 2 is a view of the electrode cap side of the cell. Cap 15 is bolted to body 1 (not shown) by bolts 17. Opening 18 of cap 15 concentrically surrounds supporting element 10 bearing electrode 8 and the portion of porous plug 20 which it does not cover, all of which are covered by membrane 16.

The effective cross-sectional area of the porous plug is generally governed by the permissible IR drop between the anode and cathode due to the charge flow as a result of the chemical reactions of the half-cells. In general, this is not a critical constraint. In the electrocells built to date the annular dimensions were I.D. 0.375 inch and O.D. 0.562 inch, with the effective length along the longitudinal axis being 0.4 inch. The effective length can range from about 0.1 inch to about 0.5 inch, or it can be as long as the body wall is thick.

As earlier stated, the arrangement of the invention finds particularly suitable use for measuring halogen residuals in aqueous systems. In these systems the membranes may be of any material which is permeable to the ion being measured, such as carbonate polymers, and olefinic polymers such as polyethylene and polypropylene. The cathode material may be gold, platinum, palladium, rhodium or cadmium while the anode may be silver, lead, mercury or thallium. The porous plug again may be of any material which is diffusible to the electrolyte. Suitable materials include natural materials such as wood (birch, maple, pine) and the synthetic materials such as carbonate polymers, olefinic polymers and copolymers, e.g., polyethylene, polypropylene, etc., which like the natural materials must be porous to the extent that they permit diffusion of the electrolyte through such to allow electrical conduction between the electrodes. The electrolyte is generally a dilute aqueous solution of salts such as potassium chloride.

A particularly effective residual chlorine cell has been produced utilizing gold as the cathode, silver as the anode, polycarbonate membrane, maple wood as the porous plug material, and potassium chloride solution as the electrolyte.

| Typical Dimensions of Standard Chlorine Cell | |
|---|---|
| Length of Cell with Cap (100) | 3 inches |
| Diameter of Cell 100 | 1.5 inches |
| Diameter of Opening 2 | .4 inch |
| Diameter of non-conductive element 10 | .375 inch |
| Diameter of electrode 8 | .3 inch |

While several embodiments in accordance with the present invention have been shown and described, it is understood that the same is not limited thereto but is susceptible of numerous changes and modifications as known to those skilled in the art, and the inventor therefore does not wish to be limited to the details shown and described herein but intends to cover all such changes and modifications as are encompassed by the scope of the appended claims.

I claim:

1. A cell for electrochemical analysis of a constituent in a sample comprising:
   an electrically nonconductive body having an electrolytic reservoir therein, said electrolytic reservoir containing an electrolyte;
   a pair of spaced electrodes, a first of said electrodes being positioned within said reservoir in contact with the electrolyte filling said reservoir;
   an opening defined in said body to provide a passageway between said reservoir and the exterior of said body;
   means closing said opening including a porous material in contact with the electrolyte in the reservoir and providing a path for electrolyte diffusion therethrough;
   said porous material comprising the sole path for transfer of electrolyte from the reservoir to the exterior of the body;
   means mounting a second of said electrodes on the exterior of the reservoir within the perimeter of said opening adjacent said porous material and being electrically coupled with the first electrode through electrolyte carried through the porous material;
   a thin, flexible polymeric membrane permeable to both said constituent and said electrolyte overlying said porous material and said second electrode; and
   cover means overlying said membrane and providing an opening through which the constituent contacts the membrane, the interchange of the constituent and the electrolyte thereby being restricted by said porous material.

2. The electrochemical cell of claim 1 and a generally cylindrical nonelectrically conductive member substantially centered within said opening, said porous material surrounding said cylindrical member, said second electrode being mounted to the end of said cylindrical member on the exterior of said body.

3. The electrochemical cell as specified in claim 2 wherein said porous material comprises an annular ring surrounding said cylindrical plug, and wherein said cover has a second opening therein, said second opening being of slightly larger diameter than said cylindrical member to limit the area of the porous material exposed to the constituent.

4. The cell according to claim 1 wherein the constituent comprises a halogen in an aqueous medium.

5. A cell according to claim 1, wherein the porous material is composed of a member selected from the group consisting of porous wood, poly olefins, and polycarbonates.

* * * * *